United States Patent [19]

Bristol

[11] Patent Number: 4,626,526

[45] Date of Patent: Dec. 2, 1986

[54] (S)-N[6]-2-HYDROXYPROPYLADENOSINES

[75] Inventor: James A. Bristol, Ann Arbor, Mich.

[73] Assignee: Warner-Lambert Company, Morris Plains, N.J.

[21] Appl. No.: 665,230

[22] Filed: Oct. 26, 1984

[51] Int. Cl.[4] .................. A61K 31/70; C07H 19/06
[52] U.S. Cl. ................................. 514/46; 536/26
[58] Field of Search ......................... 536/26; 514/46

[56] References Cited

U.S. PATENT DOCUMENTS 4,388,308  6/1983  Hamilton et al. ............. 536/26 X

OTHER PUBLICATIONS

J. Radial. Res., 15, 19 (1974), by H. Asakura et al.

Primary Examiner—Ethel G. Love
Attorney, Agent, or Firm—Joan Thierstein

[57] ABSTRACT (S)-N[6]-2-Hydroxypropyladenosines and pharmaceutically acceptable acid addition salts having highly desirable antihypertensive properties, processes for their manufacture and pharmaceutical compositions and methods for using said compounds and compositions are described.

5 Claims, No Drawings

(S)-N⁶-2-HYDROXYPROPYLADENOSINES

BACKGROUND OF THE INVENTION $N^6$-2-Hydroxypropyladenosine as a diastereomeric mixture, i.e., (R)(S)-$N^6$-2-hydroxypropyladenosine, has been reported as a radioprotective agent by H. Asakura et al., in *J. Radial. Res.*, 15, 19 (1974).

It has now been found that the (S)-diastereomer of $N^6$-2-hydroxypropyladenosine has valuable antihypertensive properties.

SUMMARY OF THE INVENTION

Accordingly, the present invention is related to an (S)-$N^6$-2-hydroxypropyladenosine derivative of the formula

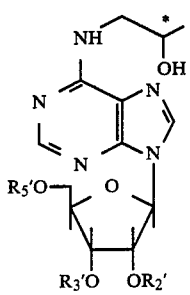

I wherein $R_2'$, $R_3'$, and $R_5'$ are each independently hydrogen, lower alkanoyl, benzoyl or benzoyl substituted by lower alkyl, lower alkoxy, halogen of trifluoromethyl, or when $R_2'$ and $R_3'$ are taken together are lower alkylidene, such as isopropylidene, or a pharmaceutically acceptable acid addition salt thereof.

The present invention also relates to a pharmaceutical composition comprising a therapeutically effective amount of a compound of the above formula I with a pharmaceutically acceptable carrier, and to a method of treating mammals by administering to such mammals a dosage form of a compound of the formula I as defined above.

DETAILED DESCRIPTION OF THE EMBODIMENTS

In the compounds of the formula I, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is O-alkyl or S-alkyl of from 1 to 6 carbon atoms as defined above for "lower alkyl".

Lower alkanoyl is a straight or branched

group of from 1 to 6 carbon atoms in the alkyl chain as defined above.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention contain asymmetric carbon atoms, and particularly, at the carbon atom connecting the hydroxy group of the $N^6$ side chain, i.e., 2-hydroxypropylamino. The invention concerns only the individual diastereomer having the pure S configuration at the carbon of the 2-hydroxypropylamino side chain. The individual diastereomer may be prepared or isolated by methods known in the art and described herein.

A preferred embodiment of the present invention includes a compound of formula I wherein $R_2'$, $R_3'$, and $R_5'$ are hydrogen, acetyl or benzoyl, or when $R_2'$ and $R_3'$ are taken together form isopropylidene.

A particular embodiment in (S)-$N^6$-(2-hydroxypropyl)adenosine.

The compounds of formula I may be conveniently synthesized by reacting a 6-halopurine riboside of formula II, wherein Hal is halogen, with (S)-2-hydroxypropylamine in an inert solvent such as alcohol, or an aprotic solvent such as dimethylformamide between about 25° to about 130° C. for from 1–48 hours.

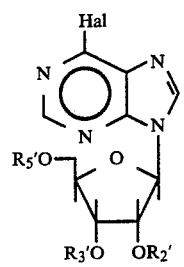

II

It is useful to add a base such as triethylamine, or calcium carbonate to neutralize the hydrogen halide formed as a byproduct of the reaction, but this can also be accomplished by using an extra equivalent of the aryl alkylamine. It is also convenient, although not necessary, to protect the ribofuranose hydroxyl groups as acetate or benzoate esters which can be removed with ammonium hydroxide or sodium methoxide following the synthesis of the $N^6$-substituted adenosine.

The compounds of formula I have been found to possess differing affinities for adenosine receptors (designated $A_1$ and $A_2$ receptors for convenience). These compounds are active in animal tests.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150–200 g) was homogenized in 30 volumes of ice-cold 0.05M Tris-HCl buffer pH 7.7 using a Brinkman Polytron PT-10, (setting number 6 for 20 seconds) and centrifuged for ten minutes at 20,000 × g (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue) versus $$\left[\frac{\text{bound radioligand}}{\text{free radioligand}}\right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the $$\log \text{ of the} \left[\frac{\text{bound radioligand}}{B_{max} - \text{bound radioligand}}\right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Arkansas). Fresh brains from male Long-Evans hooded rats (Blue Spruce Farms, Altamont, NY) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM $N^6$-cyclopentyladenosine (to eliminate $A_1$ receptor binding), 10 mM $MgCl_2$, 0.1 units/ml of adenosine deaminase and 1% dimethylsulfoxide. $N^6$-Cyclopentyladenosine was dissolved at 10 mM in 0.02 N HCl and diluted in Tris. Stock solutions and dilutions of $N^6$-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 µl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 µM, the order of additions was test compound (10 µl), $N^6$-cyclopentyladenosine (100 µl), [$^3$H]NECA (100 µl), and membranes (0.79 ml). For test compounds with $IC_{50}$ values greater than 1 µM and limited water solubility, the order of additions (same volumes) was test compound, membranes, $N^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM N⁶-cyclopentyladenosine, and specific binding was was defined as total binding minus nonspecific binding. The IC$_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the IC$_{50}$ of the drug Weighting factors were calculated under the assumption that the standard deviation was proportional to the predicted value of Y. Nonspecific binding was treated as a very large (infinite) concentration of drug in the computer analysis.

The IC$_{50}$ values (nM) for adenosine A$_1$ and A$_2$ receptor affinity for N⁶-[(S)-2-hydroxypropyl]-adenosine are 6 and 14,000, respectively.

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure: Rats were anesthetized with Telazol (1:1 tiletamine HCl and zolazepam HCl); 20-40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over-and over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, MA) by means of PE100 tubing. While on test, each rat received a continuous slow infusion of heparinized saline solution (approximately 400 1 or 40 units of heparin per 24 hour period) to prevent clot formation. Additional "flushes" of the cannula with heparinized saline were carried out when the aortic pulse pressure (systolic minus diastolic) was less than 25 mm Hg.

CADCS: The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage analysis, and report generation by the main research computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22-26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the above procedure, N⁶-[(S)-2-hydroxypropyl]adenosine produced the following changes in MAP (mean arterial pressure) and heart rate.

| | mg/kg | | Hour | | | | |
|---|---|---|---|---|---|---|---|
| | | | 1 | 3 | 5 | 7 | 9 |
| (PO) | 10 | MAP | ↓9% | ↓25% | ↓15% | ↓14% | ↓7% |
| | | HR | ↓27% | ↓48% | ↓21% | ↓1% | ↑10% |
| (IP) | 30 | MAP | ↓57% | ↓51% | ↓48% | ↓48% | ↓50% |
| | | HR | ↓71% | ↓77% | ↓79% | ↓81% | ↓83% |

The present invention further includes a method for treating hypertension in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Example further illustrates the invention.

EXAMPLE 1

$N^6$-[(S)-2-Hydroxypropyl]adenosine 7.5 g (S)(+)-1-amino-2-propanol (0.1 m), 28.63 g 6-chloropurineriboside (0.1 m) and 25 g triethylamine (0.12 m) were combined in 500 ml absolute ethanol. The mixture was refluxed for 22 hr.; upon cooling a percipitate formed. This was collected, and recrystallized in isopropanol. The product melted at 121°–124°. Analysis as ($C_{13}H_{19}N_5O_5 \cdot \frac{1}{2} C_3H_8O$). Calcd: C—49.00, H—6.52, N—19.70; Found: C—48.62, H—6.51, N 19.72.

I claim:

1. A diastereomer having the pure S configuration at the symmetric carbon of the 2-hydroxypropylamino side chain of the formula

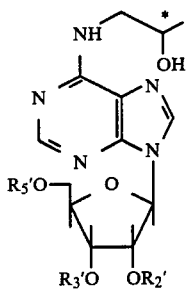

wherein $R_2'$, $R_3'$, and $R_5'$ are each independently H, lower alkanoyl, benzoyl or benzoyl substituted by lower alkyl, lower alkoxy, halogen or trifluoromethyl, or when $R_2'$ and $R_3'$ are taken together are lower alkylidene, or a pharmaceutically acceptable acid addition salt thereof.

2. A compound as claimed in claim 1, wherein $R_2'$, $R_3'$, and $R_5'$ are each H, acetyl or benzoyl, or when $R_2'$ and $R_3'$ are taken together form isopropylidene.

3. A compound as claimed in claim 2, and being (S)-$N^6$-2-hydroxypropyladenosine.

4. A pharmaceutical composition for treating hypertension comprising an antihypertensive effective amount of a compound as claimed in claim 1 together with a pharmaceutically acceptable carrier.

5. A method for treating hypertension in a mammal suffering therefrom, which comprises administering to such mammals antihypertensive amount of a compound as claimed in claim 1 in unit dosage form.

* * * * *

UNITED STATES PATENT AND TRADEMARK OFFICE
CERTIFICATE OF CORRECTION

PATENT NO. : 4,626,526
DATED : 2 DECEMBER 1986
INVENTOR(S) : JAMES A. BRISTOL

It is certified that error appears in the above—identified patent and that said Letters Patent is hereby corrected as shown below:

Column 2, line 33; Change "in" to --is--

Signed and Sealed this

Twenty-fourth Day of March, 1987

Attest:

DONALD J. QUIGG

Attesting Officer

Commissioner of Patents and Trademarks